(12) United States Patent
Hackmeister

(10) Patent No.: US 7,772,993 B2
(45) Date of Patent: Aug. 10, 2010

(54) ICING DETECTOR FOR DETECTING PRESENCE OF ICE IN STATIC AIR

(76) Inventor: Richard Hackmeister, 2631 E. Oakland Park Blvd., Fort Lauderdale, FL (US) 33306

( * ) Notice: Subject to any disclaimer, the term of this patent is extended or adjusted under 35 U.S.C. 154(b) by 228 days.

(21) Appl. No.: 11/892,149

(22) Filed: Aug. 20, 2007

(65) Prior Publication Data

US 2008/0055095 A1 Mar. 6, 2008

Related U.S. Application Data

(60) Provisional application No. 60/838,882, filed on Aug. 21, 2006.

(51) Int. Cl.
*G08B 21/00* (2006.01)
(52) U.S. Cl. ...................... 340/962; 340/583
(58) Field of Classification Search .............. 340/600, 340/612, 601, 604, 583, 581, 962
See application file for complete search history.

(56) References Cited

U.S. PATENT DOCUMENTS

| | | | | |
|---|---|---|---|---|
| 3,236,093 A * | 2/1966 | Werner | ................... | 73/431 |
| 4,797,660 A * | 1/1989 | Rein, Jr. | ................... | 340/583 |
| 4,987,296 A * | 1/1991 | Kajioka et al. | ............ | 250/222.1 |
| 5,134,380 A * | 7/1992 | Jonas | ......................... | 324/674 |
| 6,010,095 A * | 1/2000 | Hackmeister | ............. | 244/134 F |
| 6,049,282 A * | 4/2000 | MacKenzie | ................ | 340/583 |

* cited by examiner

*Primary Examiner*—Daniel Wu
*Assistant Examiner*—Rufus Point
(74) *Attorney, Agent, or Firm*—Buchanan Ingersoll & Rooney PC

(57) ABSTRACT

An icing detector is disclosed for detecting presence of ice in static air. An exemplary detector includes an ice collecting surface; a light emitter for emitting a light beam crossing an ice collecting surface, having a prismatic light manipulating window for internally-reflecting the light beam when no ice is present on the ice collecting surfaces, and externally-refracting the light when clear ice is present on the ice collecting surface, wherein the ice collecting surface is oriented to cause standing water to be directed away from the prismatic light manipulating window by gravity; a light sensor in a path of the reflected light; and an annunciator coupled to the light sensor for annunciating the presence of ice when light is sensed by the light sensor.

18 Claims, 8 Drawing Sheets

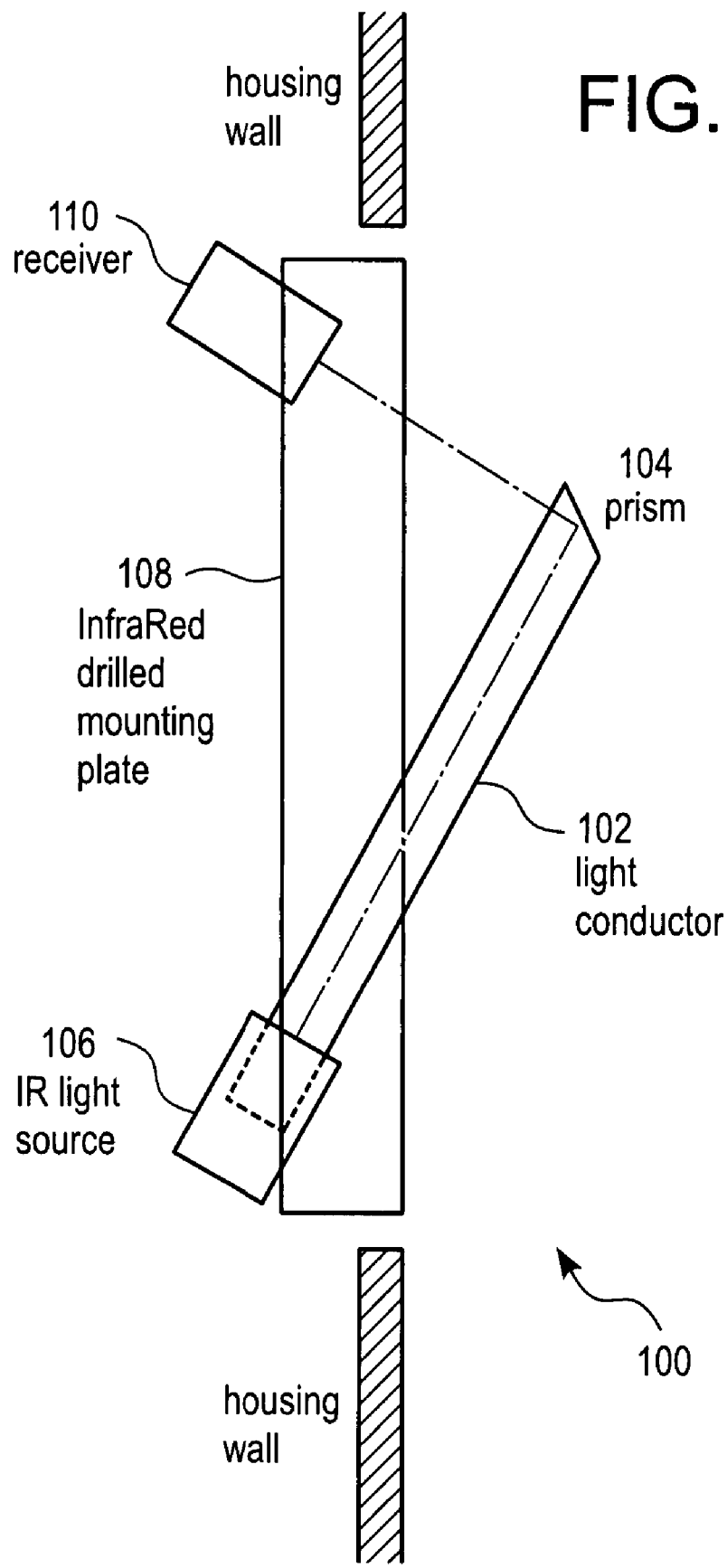

US 7,772,993 B2

ICING DETECTOR FOR DETECTING PRESENCE OF ICE IN STATIC AIR

CROSS REFERENCE TO RELATED APPLICATIONS

This application claims priority under 35 U.S.C. §119 of U.S. Provisional Application No. 60/838,882, filed Aug. 21, 2006. The entire contents of the above provisional application are hereby incorporated by reference.

BACKGROUND

U.S. Pat. No. 6,010,095 discloses a method of detecting ice in all kinds of aerospace applications. The contents of U.S. Pat. No. 6,010,095 are incorporated by reference in their entirety. An embodiment of this patent was performance tested in the world's largest icing wind tunnel at NASA Glenn in Cleveland Ohio. The tested embodiment conforms to the Society of Automotive Engineers' Aerospace Standard 5498 entitled "Minimum Operational Performance Specifications for Inflight Icing Detection Systems" core paragraph 5.2.1.1.1; and has been included in the SAE's Aerospace Information Report 4367, a compilation entitled "Aircraft Inflight Ice Detectors and Icing Rate Measuring Instruments", paragraph 4.11.

In terrestrial applications the airflow can be weak or completely still. Surface tension presented by the inside angles and radiuses of the aerospace ice detecting optics can retain standing water after the detected ice has melted away, causing false ice alerts.

SUMMARY

A sill-air precipitation sensing device is disclosed which can use gravity to rid the sensor tip of standing water.

An exemplary icing detector for detecting presence of ice in static air comprises (FIG. 1D): an ice collecting surface, light emitting means (106) for emitting a light beam crossing said light collecting surface between light conductor (102) and drilled mounting plate (108), having a prismatic light manipulating window (104) for internally reflecting said light beam through the backside of the light conductor (102) into the receiver (110) when no ice is present on the ice collecting surface, and externally refracting the light away from the receiver when clear ice is present on the ice collecting surface (104) wherein said ice collecting surface is oriented to cause standing water to be directed away from said prismatic light manipulating window by gravity; light sensing means in a path of said reflected direction; and annunciating means coupled to said light sensing means for annunciating presence of ice when light is sensed by said light sensing means.

BRIEF DESCRIPTION OF THE DRAWINGS

FIG. 1D shows an exemplary ice detector system as disclosed herein.

DESCRIPTION

Figure 1A:
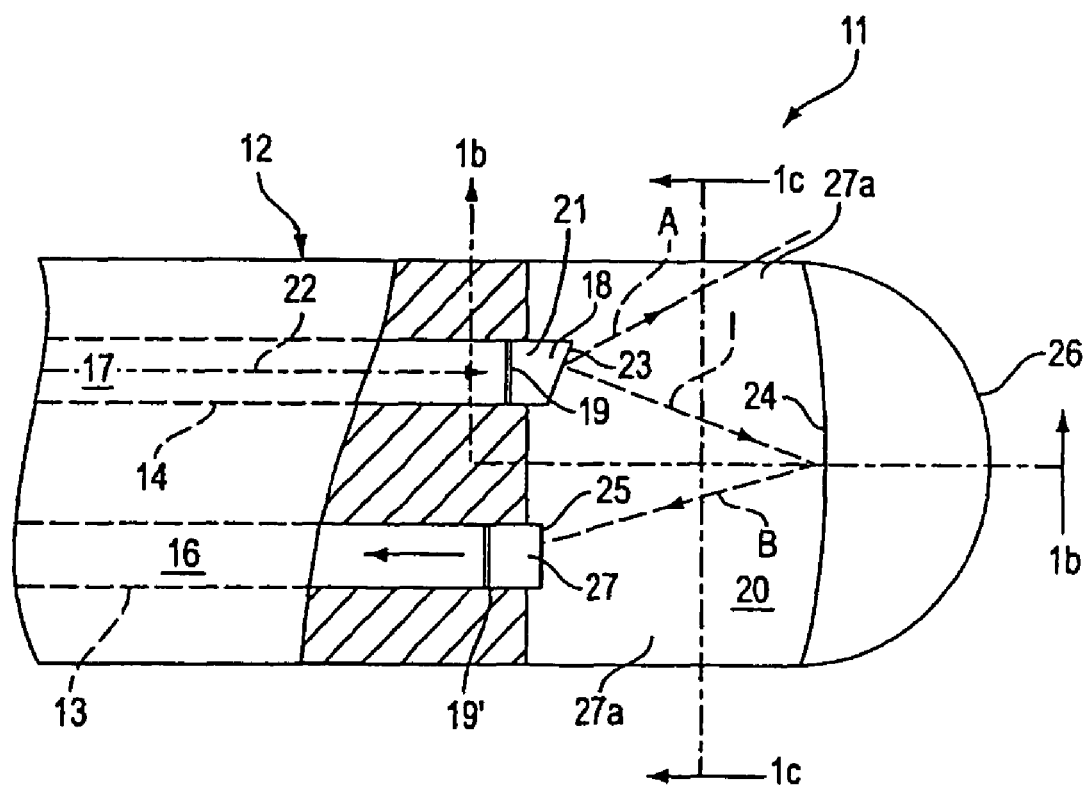
FIGS. 1A-C, 2A-2D and 3-9 show an ice detector system configured in accordance with U.S. Pat. No. 6,010,095, which can be modified in accordance with the exemplary embodiments disclosed herein.

FIG. 1D shows an exemplary icing detector 100 which includes a light conductor 102 cut at one end into a prism-face 104, and fitted with a light source at the other end. This light conductor is positioned (i.e., oriented) at an upward angle, away from other members of the detector and detector mount 108 such that the effects of gravity overcome the effects of surface tension, causing standing water to be directed away from sensor optics when in operation.

A light receiver 110 is positioned near the prism end of the fiber light conductor (e.g., configured as an optical fiber) so as to receive light energy exiting the fiber's radius as a result of internal reflection from the prism face.

The prism face of prism 104 is exposed to precipitation and the formation of clear ice, rime ice, frost, condensation, show and raindrops.

The light source 106 is energized, and the excitation signal is transmitted through the light conductor to its prism-face.

The light conductor 102, light source 106 and receiver 110 may be mounted in a mounting device 108, such as any suitable plate drilled to hold the elements in proper relation to each other. This plate may be fitted with an optional heating element 112 to de-ice the sensor if required.

Internal reflection at the prism-face causes some of the light signal to reflect and exit the fiber through the fiber's diameter, and illuminate the receiver.

Optical refraction causes some of the excitation light to exit the light conductor through the prism face and be lost. This light is captured and used in a manner as described in the aforementioned U.S. Pat. No. 6,010,095, the disclosure of which has been incorporated herein by reference.

The detector of U.S. Pat. No. 6,010,095 shown in FIGS. 1A, 1B herein can be modified to include the FIG. 1 detector 100.

Figure 1B:
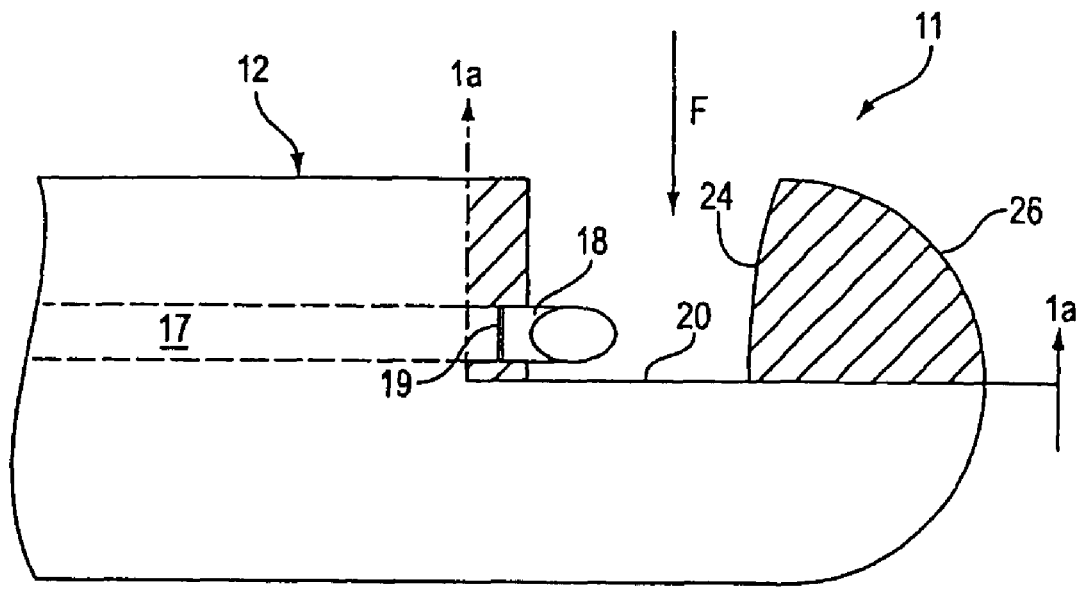

For example, FIGS. 1A and 1B show the icing detector 11 in respective partially cross-sectional views. The detector body 12 may be arranged to be mounted externally on the skin of a device (e.g., an aircraft) facing forwardly as indicated by arrow F in FIG. 1B facing the oncoming air stream when the device is in motion. The detector 11 is shown as having its cylindrical body 12 having two internal axially oriented cylindrical holes 13 and 14, each holding a respective outer end of respective light conductors 16 and 17, in the following identified respectively as the receiving and transmitting light conductor. The transmitting light conductor 17 is connected to a conveniently located light source, e.g. a light-emitting laser diode not shown in this view and then reoriented as shown in FIG. 1D. The outer end 18 of the transmitting light conductor 17 is coupled via an optical coupling layer 19 of transparent cement. The light continues through a light-transmitting body 21 from where a light beam exits through a slanted surface 23, having its normal N slanted at a given angle $\alpha$ to the axis 22 of the light transmitting body 21. As the light beam exits the light transmitting body 21 through the slanted surface 23 when no ice is present, it follows a direction substantially as indicated by arrow A, which indicates the general direction of the light when it exits into air, as will be described in more detail below in connection with FIG. 2.

An ice collecting surface 20 is formed in the detector body 12, in which ice will collect under motion (e.g., flight) in icing conditions.

If, however, clear ice is forming on the ice-collecting surface 20 and the slanted surface 23, the exiting light will be refracted by the layer of ice to follow a direction indicated by arrow 1, in which case it will increase the illumination of a reflecting surface 24 on the inside of a dome 26 projecting forwardly of the detector body 12. Due to the curvature of the reflecting surface 24, the reflected light beam indicated by arrow B is reflected back to the end 25 of the receiving light conductor 16 which can be reoriented in the manner shown in FIG. 1D. In order to provide an air and fluid-tight seal, a sealing cylinder 27 may be inserted in the outer end of the cylindrical hole 13, and coupled to the receiving light conductor 16 through a transparent sealing layer 19'. The dome 26 may advantageously have air exit openings 27a to maintain laminar flow of air from the interior of the dome 26.

Figure 1C:
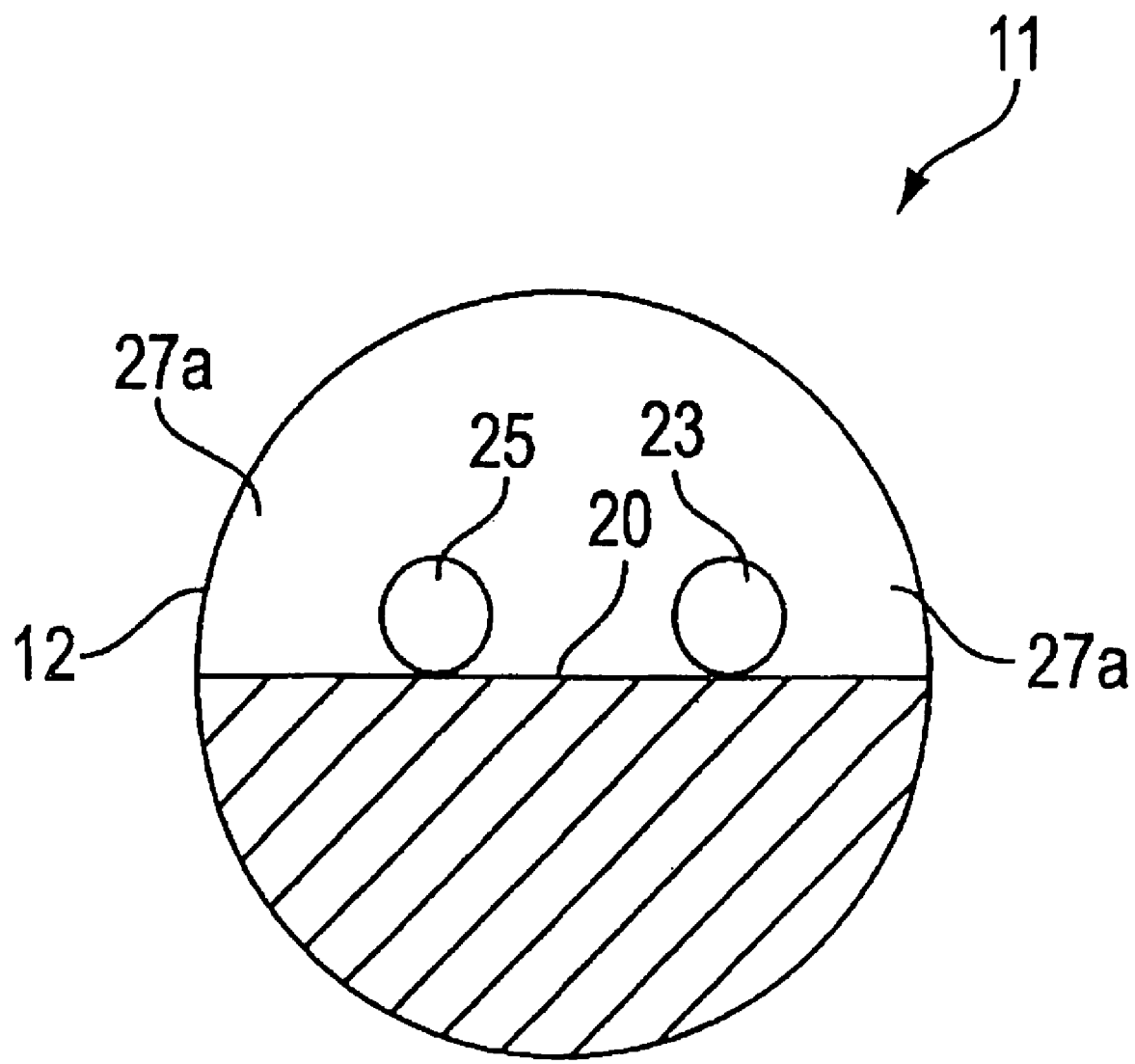

FIG. 1C is a cross-section of the detector body 12, seen along line 1c-1c of FIG. 1A.

FIG. 2 details a,b,c and d serve to illustrate the exit angle of a transmitted light beam indicated by arrow L under conditions of varying slant of the slanted exit surface 23, and presence or absence of ice or other refracting medium, such as e.g. fuel in a fuel tank or the like, ahead of the slanted prismatic window 23.

From the optical sciences it is known from the law, known as Snell's Law, that for a light beam crossing a surface at an incoming angle i, and an outgoing refracted angle r, wherein the surface divides two transparent media having different refractive indices, the following equation holds that wherein n is a constant. The refractive index is a measure of the relative velocity of light in that medium. The refractive index for water is 1.333, for air 1.00029, and for clear ice 1.31.

Figure 2D:
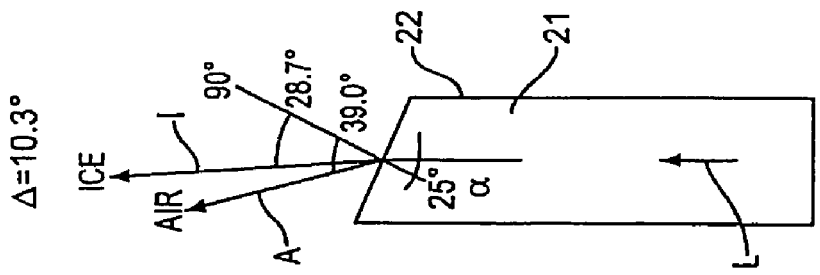
Figure 2C:
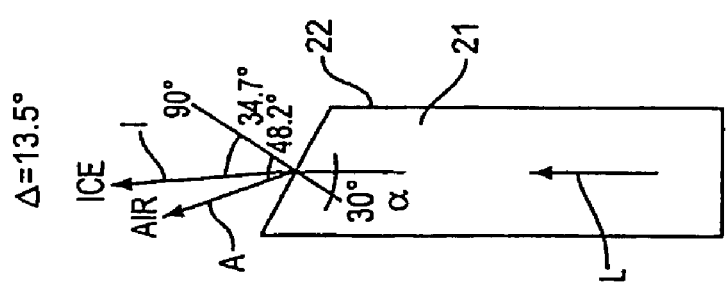
Figure 2B:
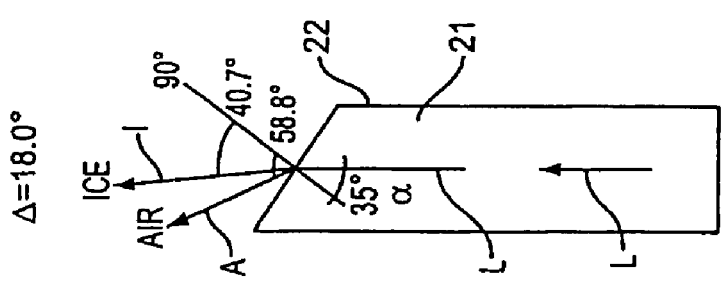
Figure 2A:
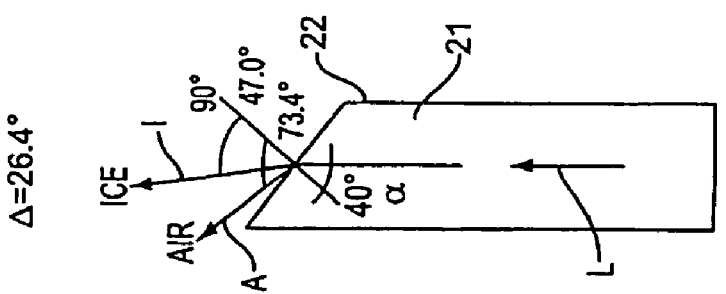

In FIG. 2A, the normal of the surface 23 to light beam L is shown as 40° angle α, while the refracted angle to a light beam I in ice is 47.0° and beam A to air 73.4°. In FIG. 2B the normal of the slanted surface is 35.degree., and the angles to refracted light beams A (air) and I (ice) from the normal are respectively 58.8° and 40.7°. In FIG. 2C angle α is 30.degree., and the angles to light beams A (air) and I (ice) are respectively 48.2° and 34.7° and in FIG. 2D respectively 39° and 28.7°.

Figure 7:
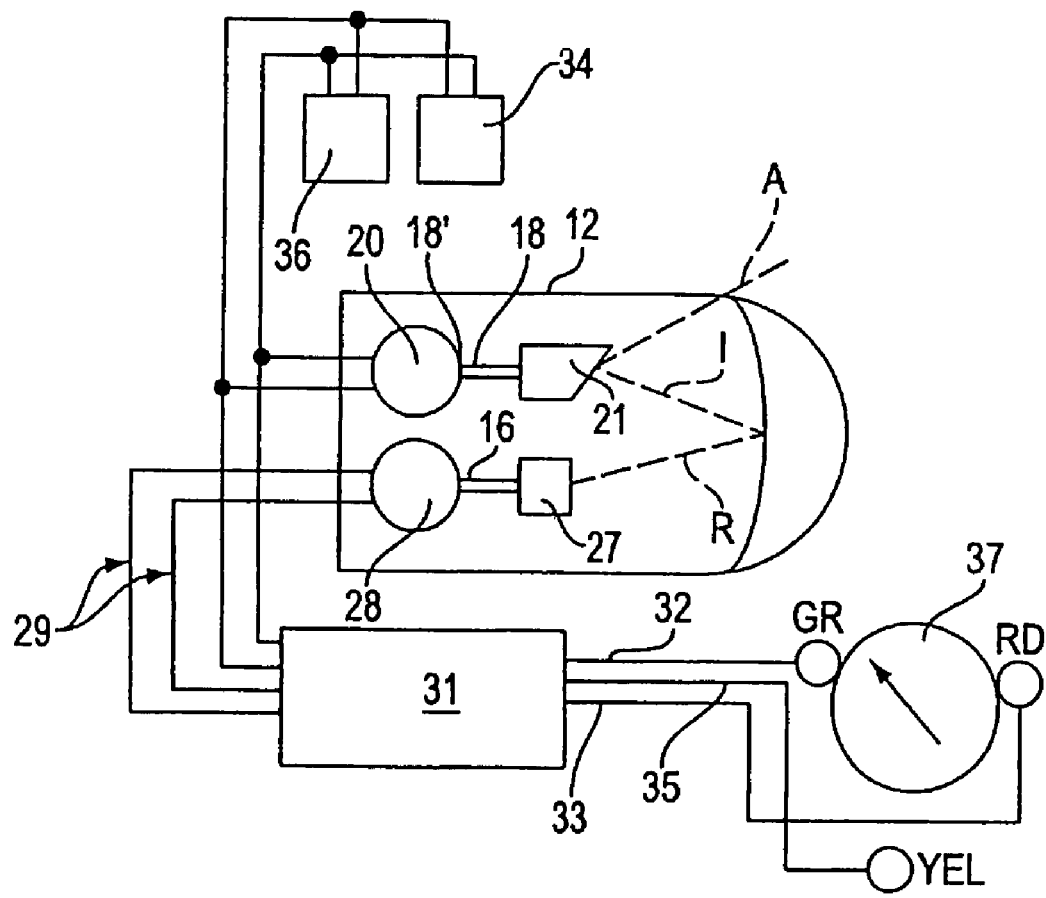
Figure 9:
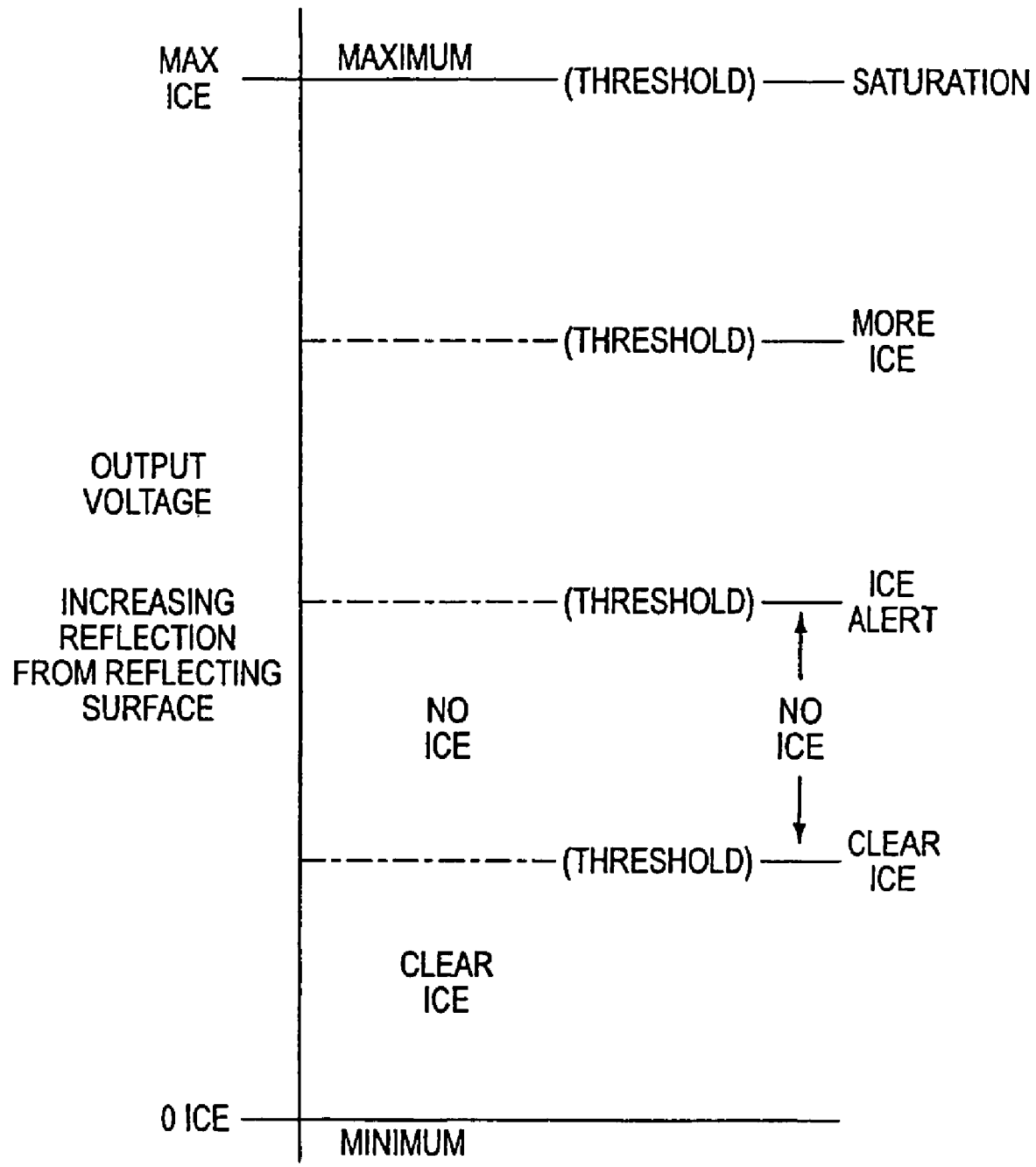

It follows that the light sensor arrangement shown in FIGS. 1A, 1B, 1C and 1D will perform as an excellent ice detector for example on a vehicle when mounted on the vehicle when pointed with its ice collecting surface 20 in direction F facing in any desired direction including, but not limited to, a possible oncoming air stream, and icing forms in the space above, i.e. forward of the light transmitting body 21. In that case, light beam I is refracted, as seen in FIG. 1A, by the ice and increases its illumination of the reflecting surface 24 back to the sealing cylinder 27 which couples the reflected light through the receiving light conductor 16 to a suitable light sensor 28 as shown in FIG. 7, which is positioned e.g. in the icing detector body 12. The light sensor 28 is connected by electric conductors 29 to an electronic discriminator circuit 31 having outputs 32, 33, 35 respectively connected to an annunciating apparatus shown as an example as LED's GR, RD and YEL, respectively indicating e.g. clear ice, rime ice and no ice. It follows that acoustic signals can be provided to augment the visual signals and/or recorded messages may be used. A vibrator connected to the control stick may also be used as an alerting indication.

The indicator lights GR, YEL and RD are preferably positioned in within the visual range of the user, e.g. within a user's peripheral visual range.

The visual indicators GR, YEL and RD may be arranged to emit light signals in various modes or patterns. In one pattern, the green light stays on in a steady light mode when no icing is present, while the red light is off. In the Icing Alert mode the green light GR goes dark while the red light RD goes on, preferably in a flashing mode. In a different pattern the red and green light both flash in an alternating mode. The yellow light YEL will be on in the no-ice condition.

A light emitter 20a, e.g. a LED diode, is optically coupled to the distal end 18' of the transmitting light conductor 18.

The electric power supply for the circuit shown in FIG. 7 is advantageously obtained from an electric storage cell 34, e.g. a NiMH cell or the like. In order to avoid drawing power from the vehicle's electric system a solar cell 36, mounted on an inside window of the aircraft may be provided to keep the storage cell 34 charged.

Figure 3:
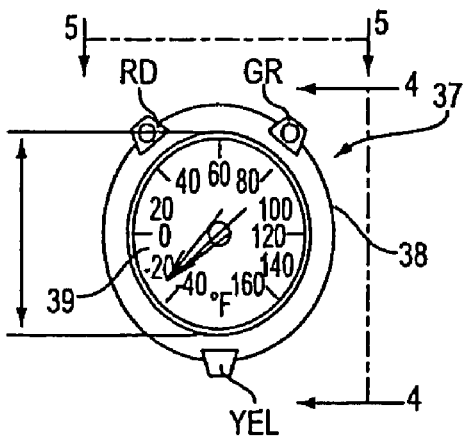
Figure 4:
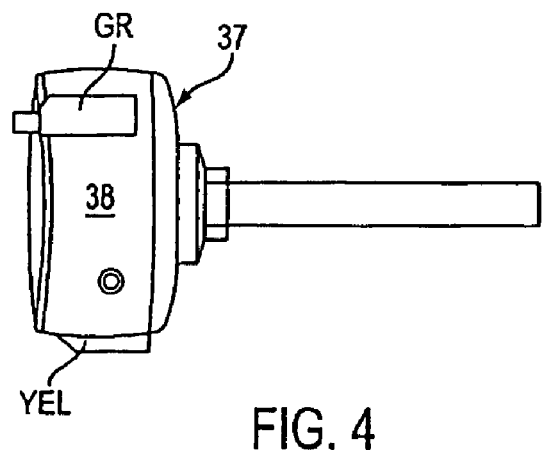
Figure 5:
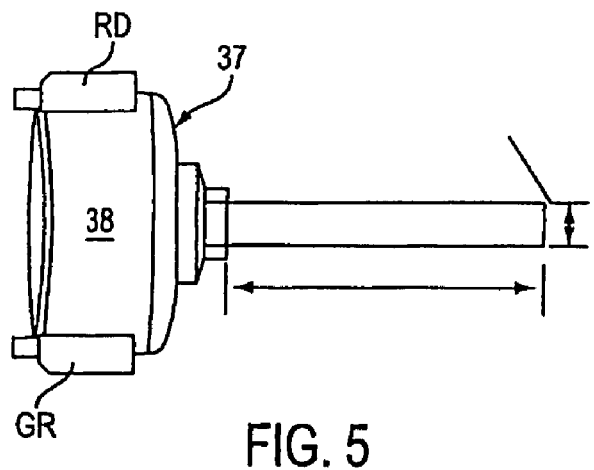

In FIG. 7 the indicator lights GR, YEL and RD are mounted on a conventional bimetallic thermometer dial 37, for example on the rim 38 of the thermometer dial 38, as shown in FIGS. 3, 4 and 5.

FIG. 3 is a face view of the thermometer dial 39, showing the light indicators RD, YEL and GR mounted forward-facing on the thermometer rim 38. FIG. 4 is a side view of the thermometer 38 seen along line 4-4 of FIG. 3. FIG. 5 is a top-down view of the thermometer 37 seen along the line 5-5 of FIG. 3, showing the light indicators RD and GR in forward facing position.

Figure 6:
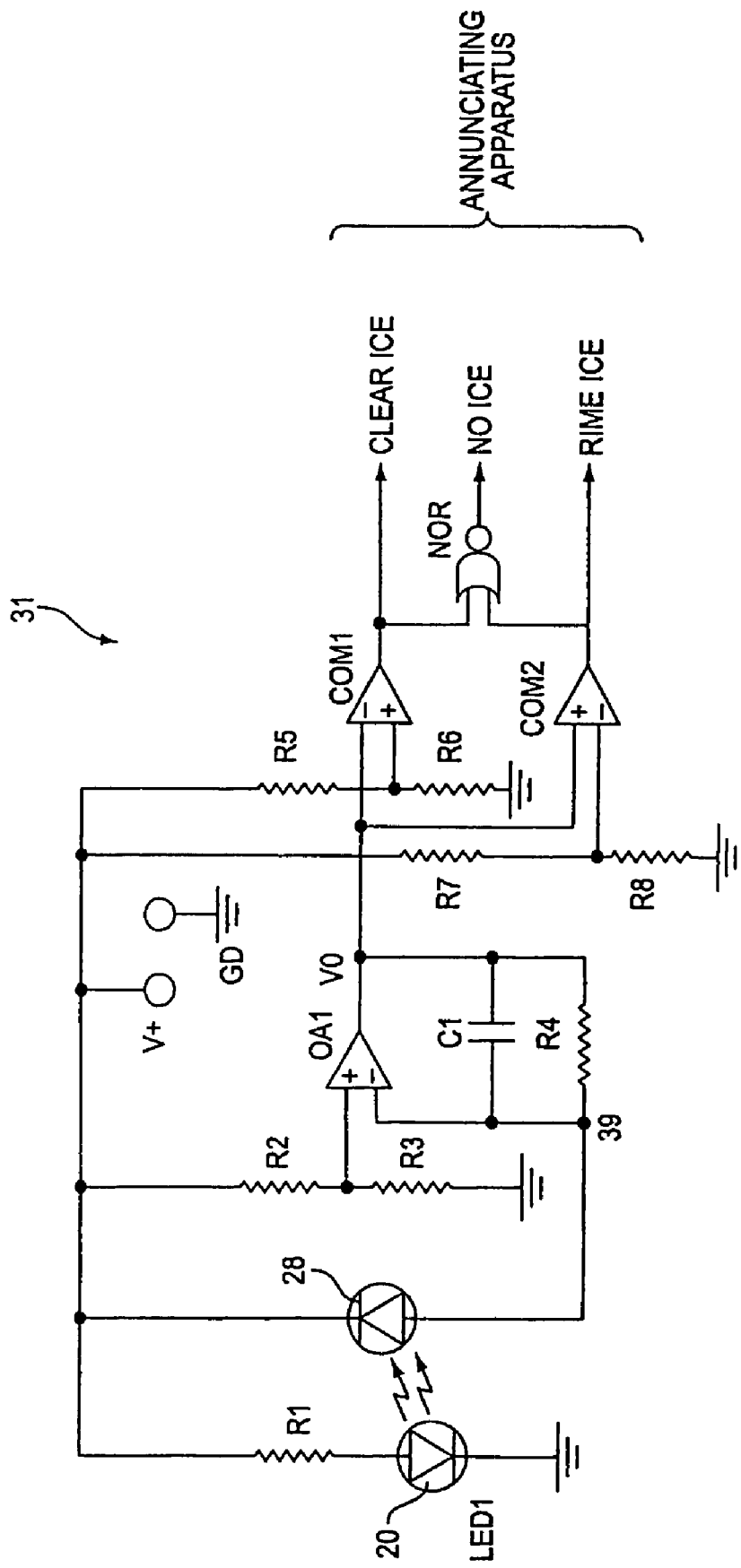
Figure 8:
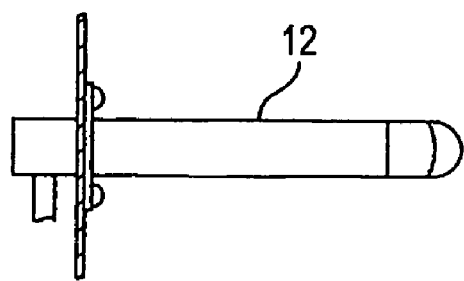

FIG. 6 is a circuit diagram of the discriminator circuit 31, wherein a light emitting diode LED1 is the light emitter or laser diode 20a shown in FIG. 7, which is coupled via light conductor 18 and the light transmitting body 21 to generate the outgoing light beam A when no ice is present or the refracted light beam I when ice is present as described above. When ice is present, the reflected light beam returns via the sealing cylinder 27 and is conducted via the receiving light conductor 16 to be detected by the light-sensing photo diode 28, as described above.

The zig-zag arrow symbol between the LED 20 and the light sensor 28 symbolizes the optical light path through the ice detector housing 12 as described above. The receiving light sensor 28 is connected to the inverting input of operational amplifier OA1, which is biased to operate as a conventional op-amp, such as type LM-741 from National Semiconductor, Inc.

When air (no ice) is present in the sensor air gap, the resistive divider R2/R3 biases the output level of OA1 to be in its mid-range. Neither COMPARATOR 1 nor COMPARATOR 2 is turned on. Both inputs to the NOR gate are false, and so its output is TRUE, indicating a no-ice state.

When clear ice is present in the air gap, the light return signal is intensified due to the additional illumination refracted onto the reflecting wall. The op-amp's output signal (Vo) therefore intensifies (actually becomes more negative, since the signal is connected to the op-amp's inverting input). Vo then crosses the detector's lower threshold established by the resistive divider R5/R6, and causes the output of COM 1 to go TRUE. This asserts the CLEAR ICE signal, and also negates the NO ICE signal from the NOR gate.

When opaque rime ice is present in the air gap, it obstructs the light return signal from the reflecting wall. The op-amp's output signal (Vo) therefore diminishes (actually becomes more positive, since the signal is connected to the op-amp's inverting input). Vo then crosses the detector's upper threshold established by the resistive divider R7/R8, and causes the output of COM 2 to go TRUE. This asserts the RIME ICE signal and negates the NO ICE signal from the NOR gate.

COM 1 and COM 2 outputs are mutually exclusive because the op-amp output signal Vo is connected to COM 1's inverting input, and to COM 2's non-inverting input.

The internally-reflected light that exits the fiber through the fiber's diameter (behind the prism-face) is used in an exemplary embodiment disclosed herein to detect various forms of precipitation by attenuation of the light signal.

Detection of rime ice, frost, condensation, snow, and other forms of opaque or translucent precipitation is effected by attenuation of the optical signal through the fiber's backside diameter which faces the receiver. The precipitation attenuates the optical signal that reflects from the inside of the prism face, through the fiber's body, and exits through the fiber's backside radius onto the detector.

Detection of clear ice, raindrops and other forms of clear precipitation is effected by optical deformation (however momentary or static) of the prism face. Precipitation contact with the optical conductor prism face (whose index-of-refraction is 1.3) with precipitating substances of similar indices-of-refraction such as raindrops (1.3) and clear ice (1.3) effectively distorts the shape of the prism face into a lens. This distortion of the prism face causes attenuation by refracted light and a reduction of the internally-reflected light signal and resultant attenuation of the optical signal as received by the receiver.

Thus modulated with information from either clear or opaque precipitations, the optical signal is converted to an electrical signal by the receiver 110, then compared to one or more references, and made available to a host system as an electrical output.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. An icing detector for detecting presence of ice in static air comprising:
   an ice collecting surface;
   light emitting means for emitting a light beam crossing said ice collecting surface, having a prismatic light refracting window for refracting said light beam in a first direction when no ice is present on the ice collecting surface and in a second direction when clear ice is present on the ice collecting surface, wherein said ice collecting surface is oriented to cause standing water to be directed away from said prismatic light refracting window by gravity;
   light sensing means in a path of said second direction; and
   annunciating means coupled to said light sensing means for annunciating presence of ice when light is sensed by said light sensing means.

2. An icing detector according to claim 1 for detecting clear ice by its index-of-refraction.

3. An icing detector according to claim 1 for detecting raindrops by their index-of-refraction.

4. An icing detector according to claim 1 for detecting at least one of frost, rime, snow and condensation by its opacity.

5. An icing detector according to claim 1 comprising:
   a heating element to de-ice the sensor.

6. An icing detector according to claim 1 for detecting individual raindrops in real time without accumulating them.

7. An icing detector according to claim 1 for detecting the moment when falling rain has turned to ice.

8. An icing detector according to claim 5 for detecting raindrops falling on top of ice.

9. An icing detector according to claim 1 including a reflecting surface disposed in said second direction for reflecting said light beam in a direction of said light sensing means.

10. An icing detector according to claim 1, wherein said light emitting means include a light source, a transmitting light conductor having a light entry end for receiving light from said light source and a light exit end forming said light refracting window.

11. An icing detector according to claim 10, including a detector body having said ice collecting surface formed therein, a first upstanding wall disposed at lone side of said ice collecting surface having said light emitting means and said light receiving means mounted therein, and a second upstanding wall disposed oppositely said first upstanding wall having said reflecting surface formed therein, facing said first upstanding wall.

12. An icing detector according to claim 10, including an electronic light sensor, wherein said light sensing means include a receiving light conductor having a light receiving end disposed in said first upstanding wall, and a light exit end coupled to said electronic light sensor, wherein said electronic light sensor is disposed away from said detector body.

13. An icing detector according to claim 11, wherein said reflecting surface is formed with a concave curvature facing said first wall for focusing said light on said light sensing means.

14. An icing detector according to claim 11, wherein said prismatic light refracting window is formed as a slanted planar cut through said first light conductor, said slanted planar cut having a normal substantially parallel with said ice collecting surface.

15. An icing detector according to claim 12, including in said light sensing means a photo diode coupled to said light exit end of said receiving light conductor, an electronic detecting circuit having an input connected to said photo diode for detecting presence of light received by said photodiode, and an output connected to an electronic circuit having a "clear ice" output, said electronic circuit operative for activating said "clear ice" output upon presence of light being sensed by said light sensing means.

16. An icing detector according to claim 5, wherein said electronic circuit includes a threshold circuit and a "rime ice" output wherein said "rime ice" output is activated when the ice sensing detector receives a light input having a light level below said threshold.

17. An icing detector according to claim 1, wherein said annunciating means are operative for annunciating in at least one of the modes:
   acoustic mode, optical display mode and vibrating mode.

18. An icing detector according to claim 1, wherein said prismatic light refracting window is formed as a slanted planar cut through a first light conductor of said light emitting means.

* * * * *